(12) United States Patent
Manigoff et al.

(10) Patent No.: US 10,349,922 B2
(45) Date of Patent: Jul. 16, 2019

(54) ON DEMAND ULTRASOUND PERFORMANCE

(71) Applicant: B-K MEDICAL APS, Herlev (DK)

(72) Inventors: Jesper Lomborg Manigoff, Frederiksberg C (DK); Michael Knud Eibye, Ballerup (DK)

(73) Assignee: B-K Medical Aps, Herlev (DK)

( * ) Notice: Subject to any disclaimer, the term of this patent is extended or adjusted under 35 U.S.C. 154(b) by 397 days.

(21) Appl. No.: 14/766,454

(22) PCT Filed: Feb. 15, 2013

(86) PCT No.: PCT/IB2013/000191
§ 371 (c)(1),
(2) Date: Aug. 6, 2015

(87) PCT Pub. No.: WO2014/125314
PCT Pub. Date: Aug. 21, 2014

(65) Prior Publication Data
US 2015/0374347 A1 Dec. 31, 2015

(51) Int. Cl.
| | |
|---|---|
| G06F 15/173 | (2006.01) |
| A61B 8/00 | (2006.01) |
| G06Q 10/06 | (2012.01) |
| G06T 1/20 | (2006.01) |
| G06F 9/50 | (2006.01) |
| A61B 8/08 | (2006.01) |

(52) U.S. Cl.
CPC ............ *A61B 8/565* (2013.01); *A61B 8/4494* (2013.01); *A61B 8/52* (2013.01); *A61B 8/54* (2013.01); *G06F 9/5044* (2013.01); *G06F 9/5055* (2013.01); *G06Q 10/06* (2013.01); *G06T 1/20* (2013.01); *A61B 8/4438* (2013.01); *A61B 8/4472* (2013.01); *A61B 8/56* (2013.01); *G06F 2209/5011* (2013.01)

(58) Field of Classification Search
CPC ...... G06F 9/00; G06F 2209/00; G06F 19/327; G06Q 10/06; G06T 1/20; A61B 8/00; A61B 8/4472
See application file for complete search history.

(56) References Cited

U.S. PATENT DOCUMENTS

| | | | |
|---|---|---|---|
| 9,317,820 B1* | 4/2016 | Todd | G06Q 10/06 |
| 9,402,601 B1* | 8/2016 | Berger | A61B 8/4472 |
| 2003/0181804 A1 | 9/2003 | Gagnon et al. | |
| 2005/0288569 A1 | 12/2005 | Battle et al. | |

(Continued)

OTHER PUBLICATIONS

International search report for PCT/IB2013/000191 published as WO 2014/125314 A1.

*Primary Examiner* — Kyung H Shin
(74) *Attorney, Agent, or Firm* — Anthony M. Del Zoppo, III; Daugherty & Del Zoppo Co., LPA

(57) ABSTRACT

An ultrasound imaging system (102) includes an ultrasound sub-system (104) with at least a transducer array (112), and an ultrasound resource pool (106). The ultrasound sub-system and the ultrasound resource pool are separate entities. The ultrasound resource pool provides temporary access to ultrasound processing resources of the ultrasound resource pool on an on-demand basis, based on an identified performance mode of the ultrasound sub-system for a scan.

19 Claims, 7 Drawing Sheets

(56) References Cited

U.S. PATENT DOCUMENTS

| | | | |
|---|---|---|---|
| 2006/0143060 A1* | 6/2006 | Conry | G06F 19/327 705/7.19 |
| 2007/0046966 A1* | 3/2007 | Mussack | G06T 1/20 358/1.13 |
| 2009/0093980 A1 | 4/2009 | Kemp et al. | |

* cited by examiner

ON DEMAND ULTRASOUND PERFORMANCE

RELATED APPLICATION

This application is a national filing of PCT application Serial No. PCT/IB2013/000191, filed Feb. 15, 2013, published as WO2014/125314 on Aug. 21, 2014. This application claims priority to PCT application Serial No. PCT/IB2013/000191, published as WO2014/125314 on Aug. 21, 2014.

TECHNICAL FIELD

The following generally relates to ultrasound and more particularly to on demand ultrasound performance, and is described with particular application to ultrasound imaging; however, the following is also amenable to one or more other ultrasound apparatuses.

BACKGROUND

Ultrasound (US) imaging has provided useful information about the interior characteristics of an object or subject under examination. An ultrasound imaging scanner has included a transducer array of one or more transducer elements that produces and transmits ultrasound signals and receives ultrasound data produced in response to the ultrasound signals interacting with structure, hardware and/or software that processes the received ultrasound data generating one or more images, and a display that visually presents the one or more images.

With a hand held ultrasound imaging scanner, the transducer array, the hardware and/or software, and the display have been housed in a same housing, which can be carried around by a user in one or both hands and utilized to scan a subject or object. In another configuration, the transducer array is included in a probe that connects, via a cable or the like and/or wirelessly, to a local computing system such as a console or the like, which includes the hardware and/or software that processes the ultrasound data and generates the images. The display may be part of the console or separate from the console and connected thereto via cable, and is used to display the images.

Unfortunately, with such ultrasound imaging scanner configurations, the consumer has had to decide on performance (e.g., low end, mid-range, high end, premium, etc.) at the time of purchase of the ultrasound imaging scanner. As a consequence, if the consumer purchases a lower end ultrasound imaging scanner, the consumer will not have the option of performing higher end scans with the lower end ultrasound imaging scanner. Alternatively, if the customer purchases a higher end ultrasound imaging scanner, the consumer will have paid a higher end price, even when the ultrasound imaging scanner is used for lower end imaging.

SUMMARY

Aspects of the application address the above matters, and others.

In one aspect, an ultrasound imaging system includes an ultrasound sub-system with at least a transducer array, and an ultrasound resource pool. The ultrasound sub-system and the ultrasound resource pool are separate entities. The ultrasound resource pool provides temporary access to ultrasound processing resources of the ultrasound resource pool on an on-demand basis, based on an identified performance mode of the ultrasound sub-system for a scan.

In another aspect, a method receiving, at an ultrasound pool, a signal identifying a performance mode of a plurality of different available performance modes of an ultrasound sub-system for a scan. The ultrasound sub-system and the ultrasound resource pool are separate entities. The method further includes temporarily allocating a sub-set of processing resources of resources of the ultrasound resource pool to the ultrasound sub-system based on the performance mode identified in the received signal for processing of ultrasound data received by the ultrasound sub-system. The method further includes de-allocating the temporarily allocated sub-set of processing resources in response to the ultrasound sub-system no longer utilizing the temporarily allocated sub-set of processing resources. The de-allocated processing resources are no longer available to the ultrasound sub-system In another aspect, a method includes receiving, by an ultrasound sub-system, data identifying a performance mode of a plurality of different available performance mode of the ultrasound sub-system for a scan. The method further includes conveying a signal indicating the identified performance mode to the ultrasound resource pool, which temporarily allocates processing resources based on the identified performance mode. The method further includes utilizing the temporarily allocated processing resources to process ultrasound data received by the ultrasound sub-system for the scan. The method further includes notifying the ultrasound resource pool that the temporarily allocated processing resources are no longer being utilized. The ultrasound resource pool de-allocates the temporarily allocated processing resources. The de-allocated processing resources are no longer available to the ultrasound sub-system.

Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which.

DETAILED DESCRIPTION

Figure 1:
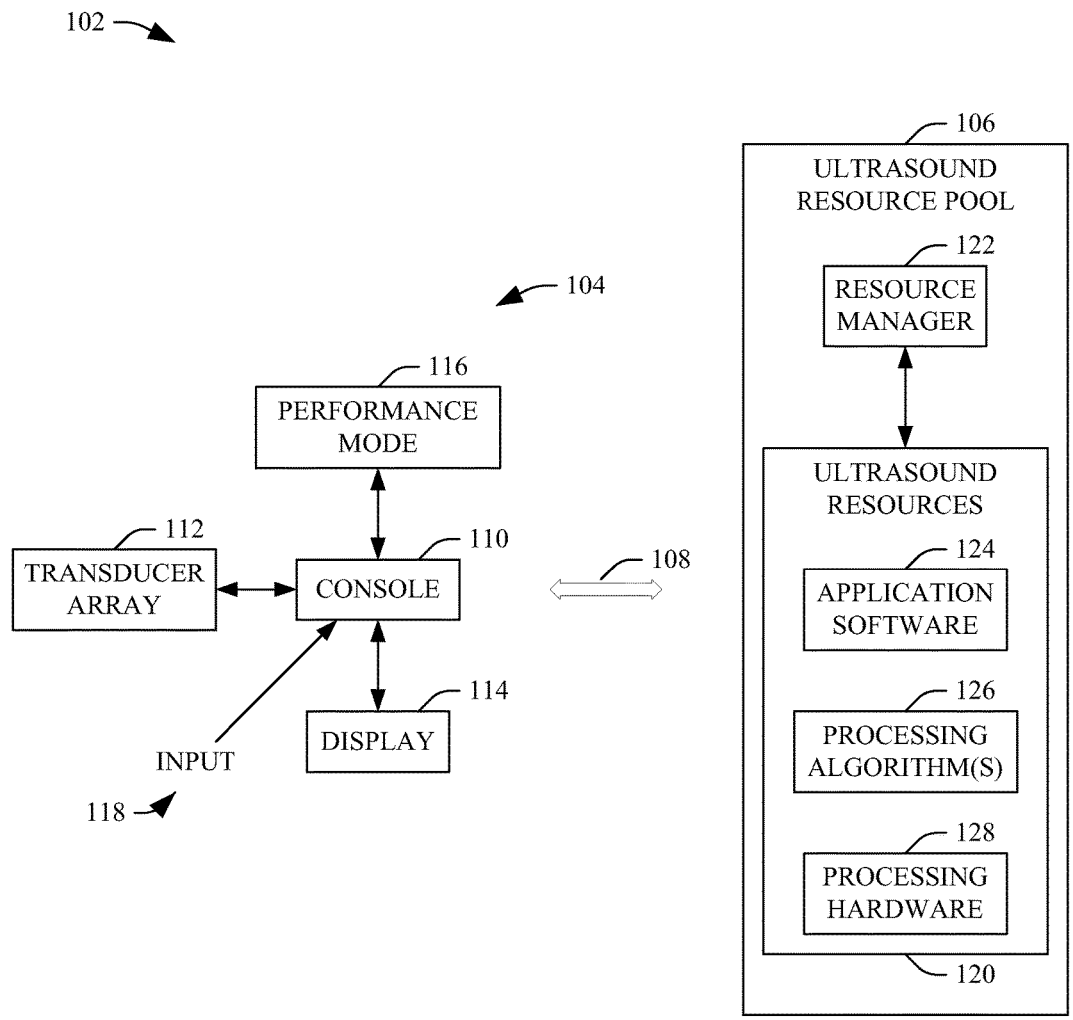
FIG. 1 schematically illustrates an example ultrasound imaging system that includes an ultrasound sub-system interfaced with a separate ultrasound resource pool, which temporarily allocates ultrasound processing resources to the ultrasound sub-system on-demand, based on a performance mode of the ultrasound sub-system.

FIG. 1 schematically illustrates an example ultrasound (US) system 102.

The ultrasound system 102 includes at least one ultrasound sub-system 104 and at least one ultrasound resource pool 106. The ultrasound sub-system 104 and the ultrasound resource pool 106 are separate entities in that they are not part of the same physical ultrasound imaging scanner. Generally, the ultrasound sub-system 104 is a physical ultrasound imaging scanner but may not include all the processing resources to process ultrasound data, whereas the pool 106 includes such processing resources.

When not being used in connection with scanning, the ultrasound sub-system 104 is not provided with access to and/or allocated processing resources of the ultrasound resource pool 106 for scanning (which includes post-processing of ultrasound data). However, when the ultrasound sub-system 104 is used in connection with scanning, the ultrasound sub-system 104, via a communications path 108, is provided with and/or allocated temporary access to utilize one or more of processing resources of the ultrasound resource pool 106 for the scanning The one or more of processing resources are de-allocated and/or released back to the ultrasound resource pool 106 when no longer utilized by the ultrasound sub-system 104.

As described in greater detail below, such access and/or allocation can be provided on an on-demand basis (e.g., before, during, and/or after scanning with the ultrasound sub-system 104) based on a performance mode (of a plurality of performance modes of the ultrasound sub-system 104) being used by the ultrasound sub-system 104 for a scan. As such, the ultrasound sub-system 104 can be used for higher and lower performance scans, with the particular resources (e.g., higher or lower performance) for the scan allocated for the scan and then de-allocated for use by other ultrasound sub-systems and/or the ultrasound sub-system 104 for another scan.

The illustrated ultrasound sub-system 104 includes a console 110, a transducer array 112, and a display 114. Where the ultrasound sub-system 104 is a hand held scanner, the console 110, the transducer array 112 and the display 114 may be housed in a same housing. Where the ultrasound sub-system 104 is not a hand held scanner, the console 110 and the transducer array 112 may be housed in a separated housings, with the display 114 either part of the console 110 apparatus or separate therefrom and in electrical communication therewith.

In the later instance, the transducer array 112 may be housed in probe or the like. The probe can include a communication port for connecting a communications cable thereto or a hard-wired communications cable. In either instance, the cable connects to the console 110. Additionally or alternatively, the probe includes a wireless interface for interfacing with the console 110. The console 110 and the display 114 may be interfaced via a wired and/or wireless communications path. Other ultrasound sub-system configurations are also contemplated herein.

The transducer array 112 includes one or more transducer elements which can be configured as a one dimensional (1D), two dimensional (2D) or other dimensional array of transducer elements. For example, the transducer array 112, in one instance, includes a 1D array of 1 to 552 (e.g., 32, 64, 192, etc.) transducer elements. In another instance, the transducer array 112 includes more transducer elements. The transducer array 112 is configured so that one or more of the transducer elements can be excited in series or parallel to transmit ultrasound signals and/or receive ultrasound data.

The console 110 includes a controller that controls excitation of the transducer elements of the transducer array 112. In one instance, this may include controlling the phasing and/or time of actuation of each of the elements, which allows for steering and/or focusing the transmitted beam from a predetermined origin along the array and at predetermined angles. The controller also can control reception of ultrasound data and can be used to focus the received ultrasound data. For example, the controller may be used to delay and sum ultrasound data from the array elements to form scanlines.

In the illustrated embodiment, the console 110 alternatively operates in one of a plurality of different performance modes 116. Identification of a particular performance mode of the performance modes 116 for operation can be through an input 118 indicative of a user performance mode of interest, an imaging protocol, etc. For example, the input 118 can be generated via a mouse click on a menu option, a button press of a physical button of a physical keyboard/keypad, activation of a touch screen area of a touch screen monitor, voice recognition, and/or otherwise.

Non-limiting examples of performance modes include low end, mid-range, high end, premium, etc., which are discussed below in greater detail. Generally, the performance modes 116 correspond to different levels of hardware and/or software. The particular set of performance modes for a sub-system 104 can be default, user defined, and/or otherwise determined The console 116 generates a signal indicating the identified performance mode for a scan, and conveys the signal to the ultrasound resource pool 106 and/or other device.

The ultrasound resource pool 106 includes ultrasound resources 120 and a resource manager 122.

The ultrasound resources 120 include a collection of application and/or processing resources that can be used in connection with the ultrasound sub-system 104 to form a complete scanner. The illustrated ultrasound resources 120 include at least one of application software 124, processing algorithms 126, or processing hardware 128. In another instance, the ultrasound resources 120 include more or less resources, including similar or different resources.

In one instance, the ultrasound resources 120 are part of a same computing device at a same location, which is separate from the ultrasound sub-system 104, as discussed herein. In another instance, the ultrasound resources 120 are distributed in that they reside at different geographical locations, are part of different computing systems, etc. Furthermore, the ultrasound resources 120 may be part of a "cloud" based system or like, such as a park(s) of interconnected servers making up computing clusters.

In one non-limiting instance, the ultrasound resources 120 are part of a network of computing resources that are accessed over a network such as the Internet, a wide area network (WAN), a local area network (LAN), and/or other network. Suitable network protocols include transmission control protocol (TCP), internet protocol (IP), Ethernet, and/or other network protocol. In this instance, the communication path 108 can be based on a wired technology (e.g., twisted pair, coaxial cable, fiber optics, etc.) and/or a wireless technology (e.g., radio frequency, cellular, satellite, etc.).

The resource manager 122 manages the application software 124, the processing algorithms 126, the processing hardware 128, and/or other resources of the pool 106. The resource manager 122 temporarily (e.g., until the ultrasound sub-system 104 is finished with them) allocates resources for the ultrasound sub-system 104 based on resources for a scan. For example, where the ultrasound sub-system 104 is operated in a higher performance mode, the resource manager 122 allocates resources suitable for higher performance, and where the ultrasound sub-system 104 is operated in a lower performance mode, the resource manager 122 allocates resources suitable for lower performance mode.

The resource manager 122, in one instance, identifies the performance mode for the ultrasound sub-system 104 based on the signal generated and conveyed by the console 110, which identifies a performance selected for the scan, the imaging protocol selected for the scan, and/or other information. Other information may include, but is not limited to, an identification of the sub-system 104, a clinician using the sub-subsystem 104, a facility at which the sub-system 104 is being used, a department within the facility at which the sub-system 104 is being used, and/or other information.

It is to be appreciated that by separating the ultrasound system 102 into an ultrasound sub-system 104 (a physical scanner) and an ultrasound resource pool 106 (cloud or other remote computing system), a consumer can purchase a single sub-system 104, without having to decide whether to purchase higher or lower end performance at the time of purchase of the sub-system 104, and then access higher or lower end performance features of the ultrasound resources 120 of the ultrasound resource pool 106 on an on-demand and/or otherwise basis for each scan performed using the ultrasound sub-system 104.

Thus, where the ultrasound sub-system 104 is operated in a lower performance mode, the resource manager 122 only needs to allocate resources that support the lower performance mode, and where the same sub-system 104 is operated in a higher performance mode, the resource manager 122 allocates resources that support the higher performance mode.

When the allocated resources are no longer needed, they can be released. This can be determined via a signal indicating the resources are no longer needed, lapse of a predetermined time duration, lack of use of the resources for a predetermined time duration, and/or otherwise. If the performance mode is changed during an imaging procedure, the allocated resources can be change to include higher or lower performance resources.

In one embodiment, the ultrasound resources 120 are accessed on a pay per use basis. With this embodiment, the resource manager 122, after determining and/or grouping the resources for a scan, can provide an estimated cost to the console 110 and/or other device, which can be accepted, rejected and/or negotiated by the requester of the resources. As actual use and/or time may not be known until after the scan is finished, the cost or final cost can be provided once the resources are released from the ultrasound sub-system 104.

In another embodiment, the ultrasound resource pool 106 is a subscription based system, fee or non-fee. This embodiment is similar to the pay per use, except that the cost for different levels of performance are determined based on the subscription level. The subscription can be confirmed based on the signal from the console 110 and/or otherwise. Non-authorized users will not be provided with access to the ultrasound resources 120. Multiple levels of subscription may be provided, offering different levels of performance.

Figure 2:
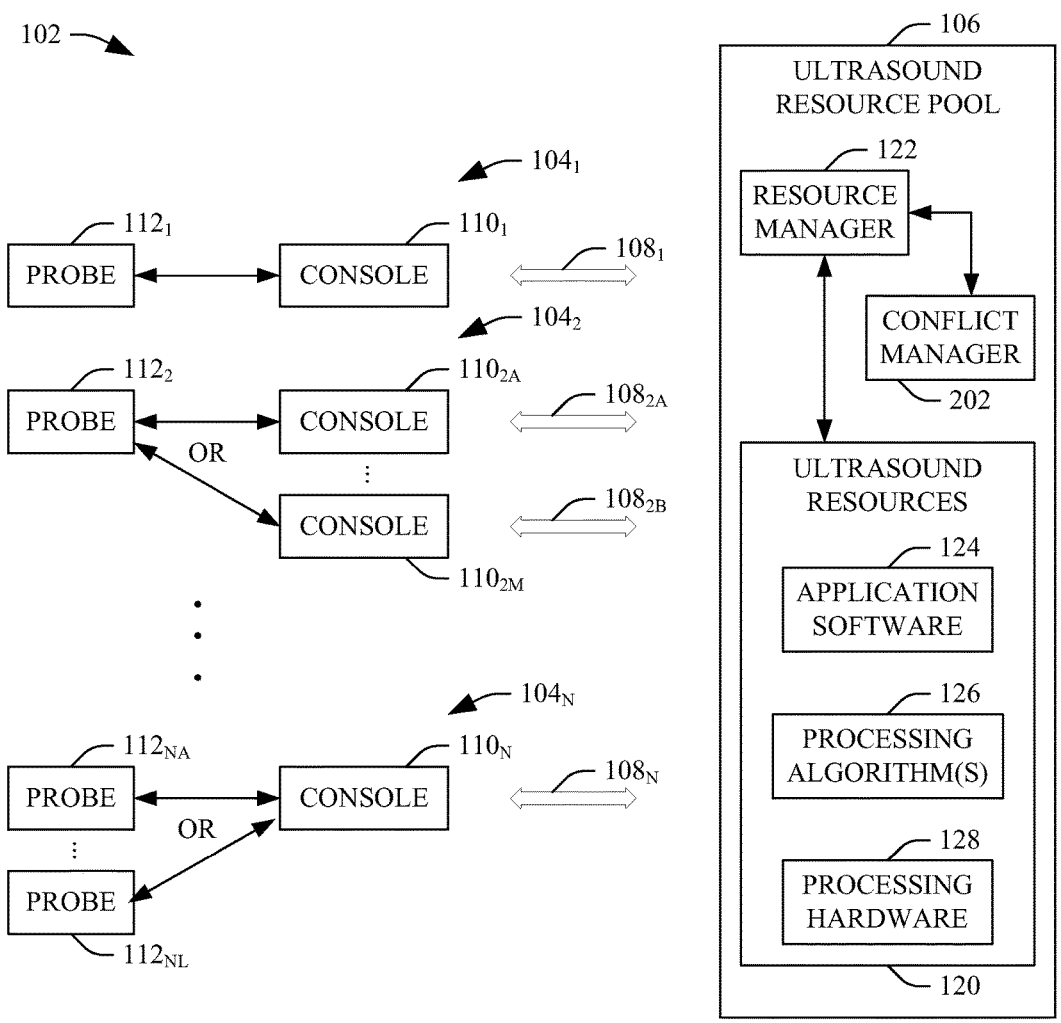
FIG. 2 schematically illustrates an example in which the ultrasound imaging system includes a plurality of ultrasound sub-systems and the ultrasound resource pool.

FIG. 2 shows an embodiment in which multiple ultrasound sub-systems $104_1, \ldots, 104_N$ share the ultrasound resources 120 of the ultrasound resource pool 106. Corresponding displays 114 and the performance modes 116 are not shown for sake for clarity, but can be included and operate similar to those discussed in connection with FIG. 1. The ultrasound sub-system $104_1$ is similar to that of ultrasound sub-system 104 described in connection with FIG. 1, with a probe $112_1$ including the transducer array probe 112, and the console $112_1$ being similar to the console 112.

The ultrasound sub-system $104_2$ is similar to that of ultrasound sub-system 104 described in connection with FIG. 1, except that a probe $112_2$ can be alternatively employed with multiple consoles $112_{2A}$ or $112_{2b}$. The consoles $112_{2A}$ or $112_{2b}$ may be substantially similar with respect to physical form (e.g., size, capabilities, etc.) but located in different locations. Alternatively, the consoles $112_{2A}$ or $112_{2b}$ vary in physical form and be located at a same location or at located in different locations.

The ultrasound sub-systems $104_N$ is similar to that of ultrasound sub-system 104 described in connection with FIG. 1, except that multiple probes $112_{2A}$ and $112_{2B}$ can be alternatively employed with a console $112_N$. The probes $112_{2A}$ and $112_{2B}$ may be substantially similar with respect to physical form (e.g., size, capabilities, etc.) but located in different locations. Alternatively, the probes $112_{2A}$ and $112_{2B}$ vary in physical form and be located at a same location or at located in different locations.

In one instance, the ultrasound sub-systems $104_1, \ldots, 104_N$ individually and sequentially access the ultrasound resources of the ultrasound resource pool 106. In another example, two or more of the ultrasound sub-systems $104_1, \ldots, 104_N$ concurrently access the ultrasound resources of the ultrasound resource pool 106. With concurrent accesses, two or more of the ultrasound sub-systems $104_1, \ldots, 104_N$ may compete for a same resource of the ultrasound resource 120.

In this embodiment, the ultrasound resource pool 106 further includes a conflict manager 202. The conflict manager 202 manages resource conflicts. For example, two or more of the ultrasound sub-systems $104_1, 104_2, \ldots, 104_N$, may be used concurrently for two high performance scans. In this instance, the two or more of the ultrasound sub-systems $104_1, 104_2, \ldots, 104_N$, may compete for the same resources which may not be available for both of the two or more of the ultrasound sub-systems $104_1, 104_2, \ldots, 104_N$. The conflict manager 202 manages such conflicts.

For example, in one instance, there may be enough resources in the ultrasound resources 120 to support two of the ultrasound sub-systems $104_1, 104_2, \ldots, 104_N$ concurrently in higher performance mode, but not three or more concurrently in higher performance mode. In instance, the conflict manager 202 decides which two are provided with access to the high performance resources. For example, the resources may be allocated in order of the request for the resources, based on a priority level (e.g., of the procedure, the department, the clinician, etc.), and/or otherwise.

The ultrasound sub-system 104 not provided with access to the higher performance resources can be notified that high performances resources are not currently available, offered a lower level of performance resources (e.g., mid-range, low end, etc.), offered to be placed in a waiting queue for the high performance resources, provided with an estimate of how long it will be before the high performance resources would become available, etc. The ultrasound sub-system 104 not provided with access may accept the lower level, send a subsequent request for higher performances resources, and/or otherwise respond, including not responding.

It is to be appreciated that the illustrated ultrasound sub-systems $104_1, 104_2, \ldots, 104_N$ are not limiting. For example, another suitable ultrasound sub-system 104 may be a combination of $104_2$ and $104_N$ with multiple probes and multiple consoles. Furthermore, the communications paths $108_{2A}$ and $108_{2B}$ may be the same or different paths, including sub-paths or channels of a same path or different paths. Furthermore, one or more of the ultrasound sub-systems $104_1, 104_2, \ldots, 104_N$ may be in communication with one or more other ultrasound resource pools 106.

Figure 3:
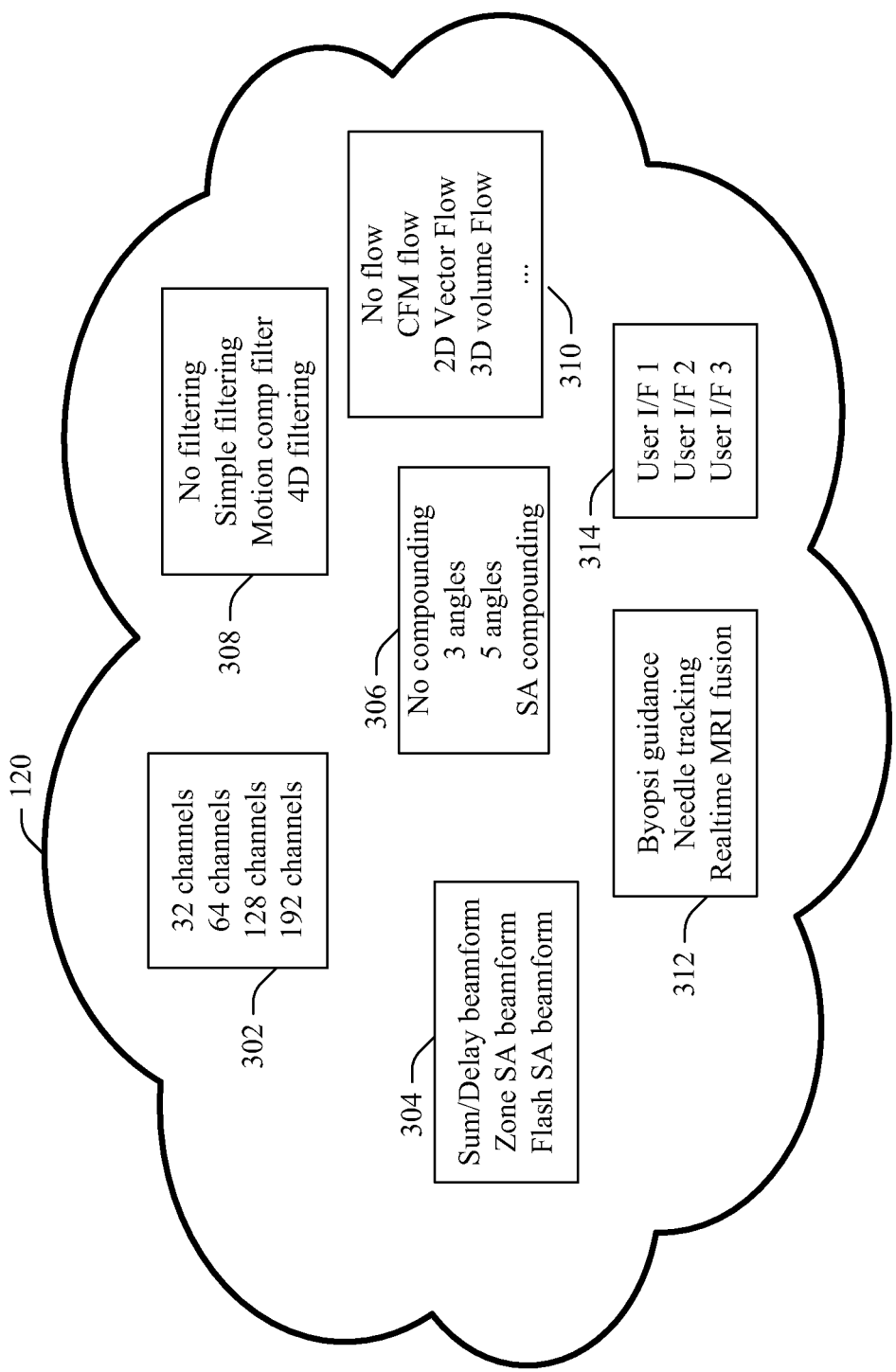
FIG. 3 schematically illustrates an example of cloud based ultrasound imaging processing resources.
Figure 4:
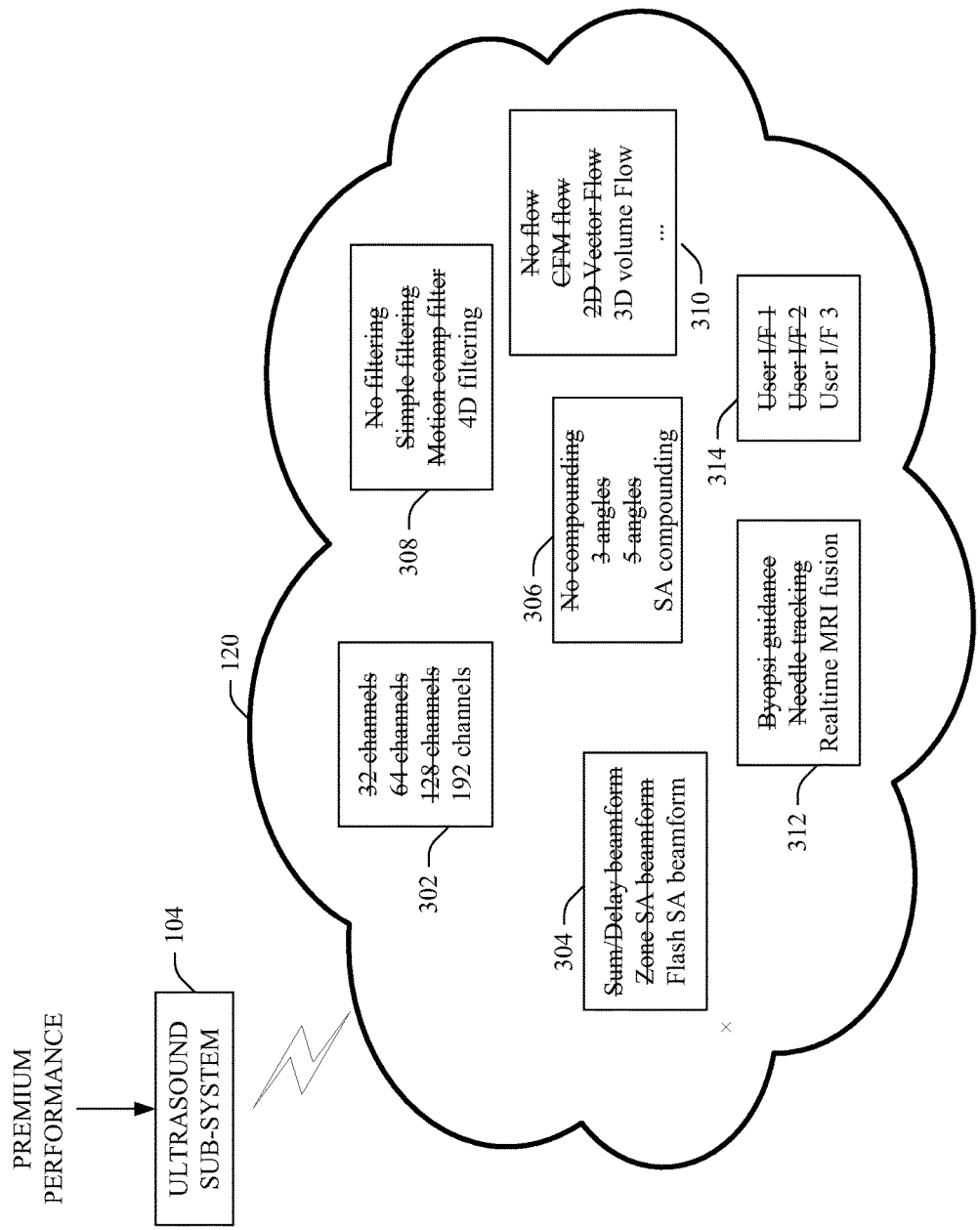
FIG. 4 schematically illustrates a single ultrasound sub-system operating in higher performance mode in connection with the cloud based ultrasound imaging processing resources.
Figure 5:
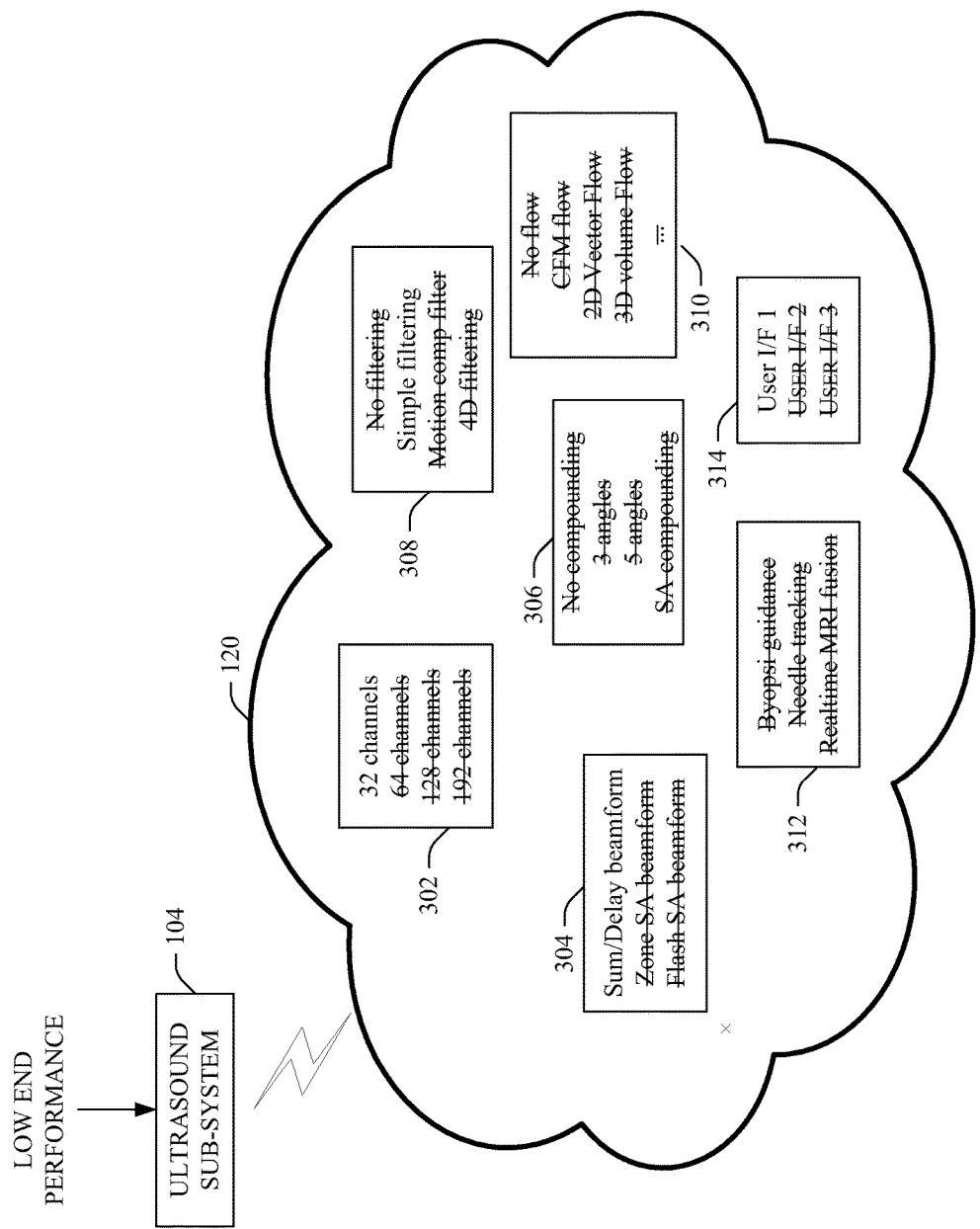
FIG. 5 schematically illustrates a single ultrasound sub-system operating in lower performance mode in connection with the cloud based ultrasound imaging processing resources.

FIGS. 3, 4 and 5 show example use case scenarios in which a single ultrasound sub-system 104 is operated in premium performance mode (FIG. 4) and low end performance mode (FIG. 5) utilizing available resources (FIG. 3) from a cloud or computer cluster based ultrasound resource pool 106 (FIGS. 3, 4 and 5).

Beginning with FIG. 3, the ultrasound resources 120 include the following resources: channel support 302:32, 64, 128 and 192 channels; beamforming 304: sum/delay, zone synthetic aperture, and flash synthetic aperture; compounding 306: none, 3 angle, 5 angle, and synthetic aperture; filtering 308: none, simple, motion compensation, 4D; flow imaging 310: none, color flow mapping, 2D vector flow, 3D volume flow; additional features 312: biopsy guidance, needle tracking, real-time MRI fusion; and user interfaces 314: I/F 1, I/F 2 and I/F 3, which represent different devices (e.g., desktop, tablet, etc.) and/or how data is presented. It is to be understood that the foregoing examples are provided for explanatory purposes and are not limiting.

Turning to FIG. 4, a single ultrasound sub-system $104_j$ is being operated in "premium" performance mode. The ultrasound sub-system $104_j$ conveys the signal indicating this mode to the resource manager 122 (FIGS. 1 and 2) of ultrasound resource pool 106 (FIGS. 1 and 2). The resources manager 122 provides the following resources of the resources 120 to the single ultrasound sub-system $104_j$: 192 channels, flash synthetic aperture beamforming, synthetic aperture compounding, 4D filtering, 3D volume flow imaging, real-time, and I/F 3. Likewise, it is to be understood that the foregoing examples are provided for explanatory purposes and are not limiting.

Although the highest performance in each category is allocated to the single ultrasound sub-system $104_j$, where high performance in all categories is not requested and/or needed, the resources in those categories are allocated accordingly, e.g., none where none are requested and/or needed and lower performance where only lower performance is requested and/or needed.

Moving to FIG. 5, a single ultrasound sub-system $104_j$ is being operated in "lower end" performance mode.

Again, the ultrasound sub-system $104_j$ conveys the signal indicating this mode to the resource manager 122 (FIGS. 1 and 2) of ultrasound resource pool 106 (FIGS. 1 and 2). The resources manager 122 provides the following resources to the single ultrasound sub-system $104_j$: 32 channels, sum/delay beamforming, simple filtering, and I/F 1. Similarly, it is to be understood that the foregoing examples are provided for explanatory purposes and are not limiting.

Likewise, although the lowest performance in a sub-set of the categories is allocated to the single ultrasound sub-system $104_j$, where higher performance is request in at least one of the categories, the resources in that category are allocated accordingly. In addition, low end performance from all the categories can alternatively be provided, where requested and/or needed.

With respect to FIGS. 4 and 5, in one instance, the allocated resources can be dynamically changed. For example, where a procedure starts off using lower performance mode and then switches to a higher performance mode, the resources allocated to the ultrasound sub-system 104 change accordingly, based on availability, and are allocated as described herein and/or otherwise.

Figure 6:
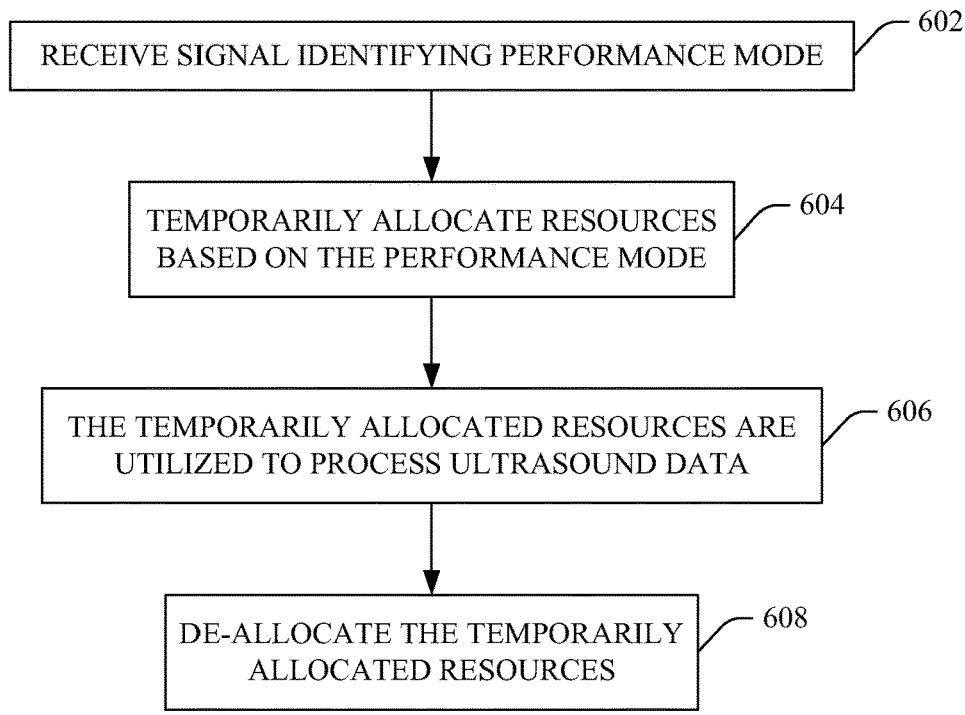
FIG. 6 illustrates an example method in accordance with the ultrasound resource pool.
Figure 7:
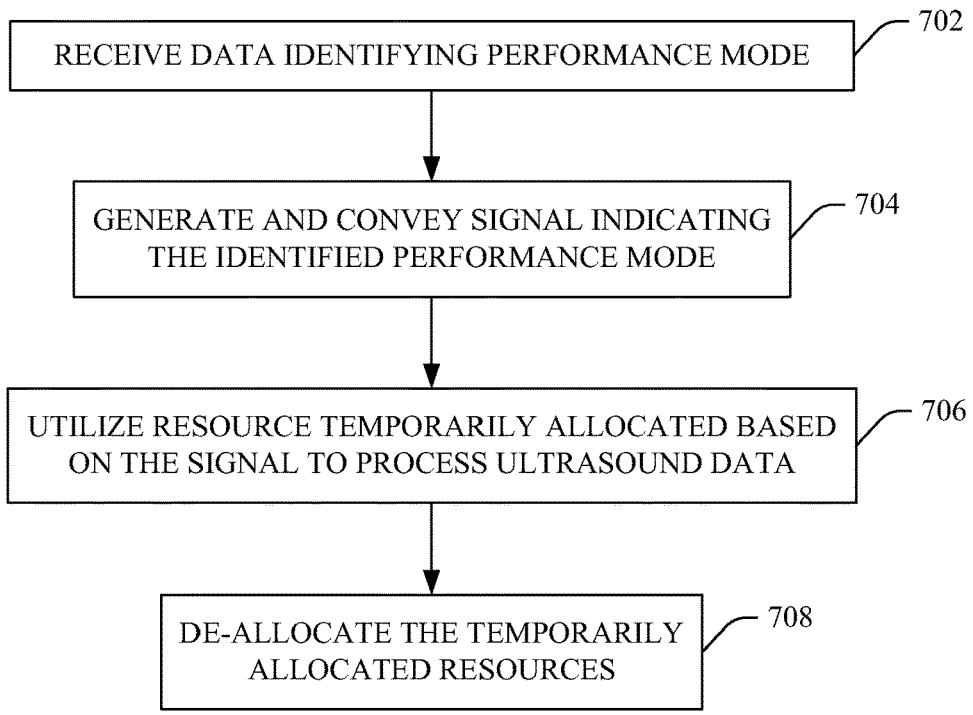
FIG. 7 illustrates an example method in accordance with the ultrasound sub-system.
Figure 8:
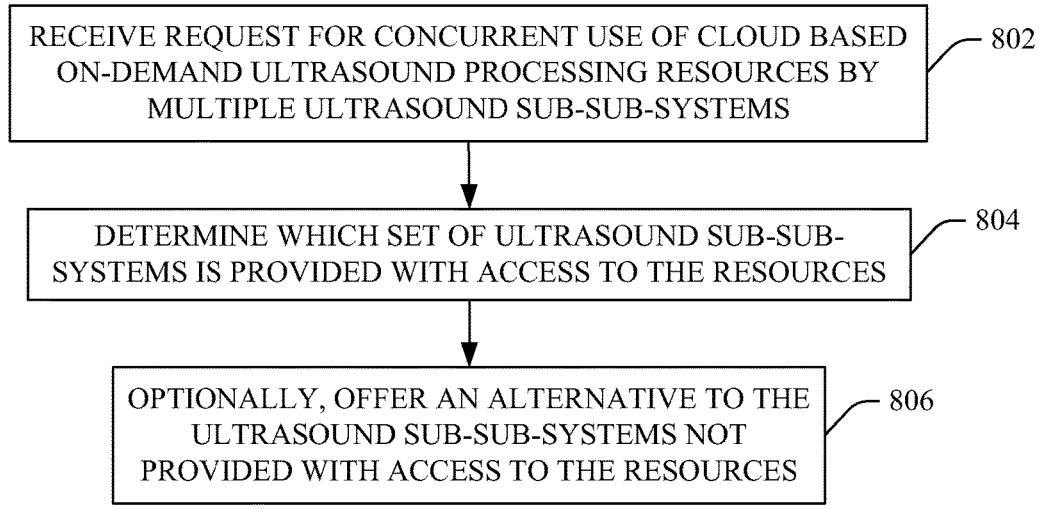
FIG. 8 illustrates an example method in accordance with the ultrasound imaging system.

FIGS. 6, 7, and 8 illustrate example methods in accordance with the description herein.

It is to be appreciated, for any or all of the methods, that the order of the acts is provided for explanatory purposes and is not limiting. As such, one or more of the acts may occur in a different order. Furthermore, one or more of the acts may be omitted and/or one or more additional acts may be added.

Initially referring to FIG. 6, an example method is described.

At 602, a signal identifying a performance mode of a plurality of different available performance modes of an ultrasound sub-system 104 for a scan is received by the ultrasound resource pool 106. The signal can be conveyed by the ultrasound sub-system 104 to the ultrasound resource pool 106 as described herein and/or otherwise.

At 604, the resource manager 122 of the ultrasound resource pool 106 temporarily allocates resources of the resources 120 of the ultrasound resource pool 106 to the ultrasound sub-system 104 based on the performance mode identified in the received signal.

At 606, the temporarily allocated resources are utilized by the ultrasound sub-system 104 performing a scan.

At 608, the resource manager 122 de-allocates or releases the temporarily allocated resources of the resources 120 back to the resources 120 in response to the ultrasound sub-system 104 no longer utilizing the resources. This can be determined through a notification signal, lack of using the processing resources, and/or otherwise.

Turning to FIG. 7, another example method is described.

At 702, data identifying a performance mode of a plurality of different available performance mode of an ultrasound sub-system 104 for a scan is received by ultrasound sub-system 104. The data can be generated by a user action (e.g., selection of a protocol, identification of the performance, etc.) as described herein and/or otherwise.

At 704, the ultrasound sub-system 104 conveys a signal indicating the performance mode to the ultrasound resource pool 106.

At 706, the ultrasound sub-system 104 utilizes resources of the ultrasound resource pool 106, which are temporarily allocated by the ultrasound resource pool 106 based on the performance mode identified in the signal.

At 708, the ultrasound sub-system 104 indicates that it no longer desires the allocated resources, which are then de-allocated or released backs to the ultrasound resource pool 106. This can be through a notification signal, no longer using the processing resources, and/or otherwise.

Next, another example method is described in connection with FIG. 8.

At 802, the resource manager 122 of a cloud based on-demand ultrasound resource pool 106 receives requests from multiple ultrasound sub-systems 104 for a same set of resources, which cannot be concurrently shared by all of the multiple ultrasound sub-systems 104.

At 804, the conflict manager 202 determines a sub-set of the multiple ultrasound sub-systems 104, which is provided with access to the set of resources, where the sub-set of the multiple ultrasound sub-systems 104 can be concurrently shared by the sub-set of the multiple ultrasound sub-systems 104 and the other multiple ultrasound sub-systems 104 are not provided with access to the set of resources.

At 806, optionally, the conflict manager 202 offers an alternative to the set of resources for the multiple ultrasound sub-systems 104 which are not provided with access to the set of resources.

Figure 9:
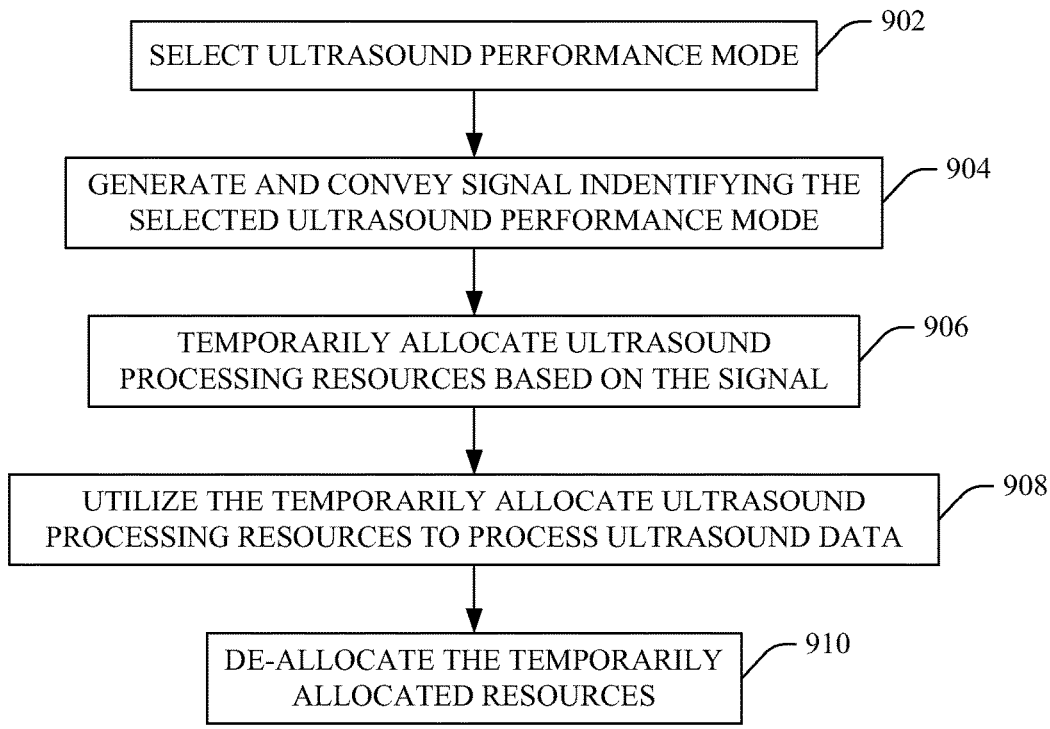
FIG. 9 illustrates example operation in accordance with the ultrasound imaging system.

Example operation is illustrated in connection with FIG. 9.

At 902, a user employing an ultrasound sub-system 104 selects a performance mode. This can be achieved by directly selecting the mode or indirectly, for example, by selecting an imaging protocol that identifies a performance mode for the protocol.

At 904, the ultrasound sub-system 104 generates a signal identifying the mode and conveys the signal to the ultrasound resource pool 106.

At 906, the resource manager 122 of the ultrasound resource pool 106 temporarily allocates resources of the resources 120 of the ultrasound resource pool 106 to the ultrasound sub-system 104 based on the performance mode identified in the received signal.

At 908, the ultrasound sub-system 104 utilizes the temporarily allocated resources of the ultrasound resource pool 106 for a scan.

At 910, the temporarily allocated resources of the resources are de-allocated in response to the ultrasound sub-system 104 no longer requesting the resources.

The above may be implemented in connection with computer readable instructions, encoded or embedded on computer readable storage medium, which, when executed by a computer processor(s), cause the processor(s) to carry out one or more of the described acts. Additionally or alternatively, at least one of the computer readable instructions is carried by a signal, carrier wave or other transitory medium.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. An ultrasound imaging system, comprising:
   an ultrasound scanner, including:
   at least a transducer array with one or more transducer elements;
   a console with a processor configured to control, based on a user input to the console indicative of a-one of a plurality of predefined performance modes for a scan, excite the transducer elements to transmit ultrasound signals and receive ultrasound data, wherein the performance mode is one of a low end, mid-range, high end, premium performance mode, default mode, or user defined mode and a different set of processing resources corresponds to each of the performance modes; and
   a display configured to display an ultrasound image; and
   one or more remote computers with an ultrasound resource pool, wherein the ultrasound scanner and the one or more remote computers are separate structures, and wherein the one or more remote computers provides temporary access to the ultrasound scanner, via a network, to a set of predefined ultrasound processing resources of the ultrasound resource pool on an on-demand basis based on the one predefined performance mode of the ultrasound scanner for the scan.

2. The system of claim 1, wherein the performance mode is identified based on an imaging protocol of the ultrasound scanner for the scan.

3. The system of claim 1, wherein the ultrasound scanner does not include the temporarily allocated ultrasound processing resources.

4. The system of claim 1, wherein the ultrasound resource pool de-allocates the ultrasound processing resources in response to the ultrasound scanner no longer employing ultrasound processing resources.

5. The system of claim 4, wherein the ultrasound scanner does not have access to the de-allocated ultrasound processing resources.

6. The system of claim 1, wherein the one or more computers are part of a cloud based resource pool.

7. The system of claim 1, wherein the one or more computers are part of one or more groups of interconnected computing systems.

8. The system of claim 1, the ultrasound resource pool, comprising:
   a conflict manager that manages a resource conflict between the ultrasound scanner and at least one other ultrasound scanner competing for a same set of processing resources.

9. The system of claim 8, where the conflict manager allocates the set of resources to one of the ultrasound scanner and the at least one other ultrasound scanner and not the other.

10. The system of claim 9, where the conflict manager allocates the set of resources based on one of an order of request or a predetermined priority level of the scan.

11. A method, comprising:
   receiving, at an ultrasound pool, a signal identifying a performance mode of a plurality of different available performance modes of an ultrasound sub-system for a scan, wherein the ultrasound sub-system and the ultrasound resource pool are separate entities;
   temporarily allocating a sub-set of processing resources of resources of the ultrasound resource pool to the ultrasound sub-system based on the performance mode identified in the received signal for processing of ultrasound data received by the ultrasound sub-system, wherein the performance mode is one of a low end, mid-range, high end, premium performance mode, default mode, or user defined mode, and a different set of processing resources corresponds to each of the performance modes; and
   de-allocating the temporarily allocated sub-set of processing resources in response to the ultrasound sub-system no longer utilizing the temporarily allocated sub-set of processing resources, wherein the de-allocated processing resources are no longer available to the ultrasound sub-system.

12. The method of claim 11, wherein the ultrasound sub-system does not include the temporarily allocated ultrasound processing resources.

13. The method of claim 11, wherein the ultrasound processing resources are part of a cloud based resource pool.

14. The method of claim 11, wherein the ultrasound processing resources are part of one or more groups of interconnected computing systems.

15. A method, comprising:
receiving, by an ultrasound sub-system, data identifying a performance mode of a plurality of different available performance mode of the ultrasound sub-system for a scan;
conveying a signal indicating the identified performance mode to the ultrasound resource pool, which temporarily allocates processing resources based on the identified performance mode, wherein the ultrasound sub-system and the ultrasound resource pool are separate entities, wherein the performance mode is one of a low end, mid-range, high end, premium performance mode, default mode, or user defined mode, and a different set of processing resources corresponds to each of the performance modes;
utilizing the temporarily allocated processing resources to process ultrasound data received by the ultrasound sub-system for the scan; and
notifying the ultrasound resource pool that the temporarily allocated processing resources are no longer being utilized, wherein the ultrasound resource pool de-allocates the temporarily allocated processing resources, and the de-allocated processing resources are no longer available to the ultrasound sub-system.

16. The method of claim 15, wherein the ultrasound sub-system does not include the temporarily allocated ultrasound processing resources.

17. The method of claim 15, wherein the ultrasound processing resources are part of a cloud based resource pool.

18. The method of claim 15, wherein the ultrasound processing resources are part of one or more groups of interconnected computing systems.

19. The method of claim 15, wherein the data is generated by a user action identifying the performance mode.

* * * * *